United States Patent [19]

Agustin

[11] Patent Number: 5,168,264
[45] Date of Patent: Dec. 1, 1992

[54] POSTURE POSITION SENSOR

[76] Inventor: Hermenegildo C. Agustin, 343 Regents Park Dr., Vallejo, Calif. 94591

[21] Appl. No.: 846,837

[22] Filed: Mar. 6, 1992

[51] Int. Cl.⁵ .............................................. G08B 21/00
[52] U.S. Cl. ................................ 340/573; 200/61.52; 200/DIG. 2; 340/689
[58] Field of Search ............................. 340/573, 689; 200/61.52, DIG. 2

[56] References Cited

U.S. PATENT DOCUMENTS

| | | | |
|---|---|---|---|
| 4,871,998 | 10/1989 | Chaillou | 340/573 |
| 4,938,476 | 7/1990 | Brunelle et al. | 340/573 |
| 4,958,145 | 9/1990 | Morris | 340/573 |

Primary Examiner—Glen R. Swann, III
Attorney, Agent, or Firm—Limbach & Limbach

[57] ABSTRACT

An electronic posture position sensor device for alerting the user whenever an incorrect posture is assumed. The posture position sensor includes an electrical circuit that includes, a power means, a switch assembly, an electronic timer capable of being set at predetermined cycles, and an alerting means. The switch assembly comprises a first conducting pendulum and two sensor terminals attached, respectively, to second and third selectively positionable conducting pendulums. The second and third pendulums have a clamping means which allow the user to manually position the second and third pendulums for different sitting positions. When an incorrect posture is assumed, the switch assembly is opened which allows current to flow from the power means through the circuit to the timer. When the predetermined timer cycle elapses, the current causes the alert means to alert the user when sitting in an incorrect sitting position.

10 Claims, 2 Drawing Sheets

POSTURE POSITION SENSOR

TECHNICAL FIELD OF THE INVENTION

The present invention relates to an electronic device designed to monitor the sitting position of the user's torso and to alert the user whenever an incorrect posture is assumed.

BACKGROUND OF THE INVENTION

Correct sitting position continues to be a significant health concern for today's office worker. In a given day, an officer worker may sit up to seven hours. Attempts to correct one's sitting posture usually fail because the mind simply cannot remain vigilant while it attends to numerous other tasks in the work environment. If one was automatically alerted each time he or she drifted back to a slouching posture, then that person would have a reasonable chance of reversing the habit.

Current devices provide a means for alerting the individual wearing the device of incorrect posture. However, these devices do not permit the individual wearing the device to easily define the boundaries of incorrect sitting positions by simply pressing two buttons. The devices currently used require the use of a tool and disassembly of the device. This is disadvantageous because the user must remove the device in order to adjust the device, he or she must have access to a tool such as a screw driver, and there is a possibility of disrupting the circuitry of the device by disassembling it.

The importance of being able to adjust the boundaries of movement is that it allows the individual's sitting position to deviate a preselected amount from the upright position without triggering the alerting mechanism. This would allow the device to be easily and quickly adjusted for erect sitting positions in a chair and for relaxed or reclined positions such as sitting on a couch or in an automobile. This adjustability also allows the device to be individually set for each user based upon the natural torso configuration of that user and for specific circumstances.

SUMMARY OF THE INVENTION

It is therefore an object of the present invention to provide a posture position sensor that can alert the user whenever their posture deviates a predetermined amount from the upright and/or relaxed positions.

It is another object of the present invention to provide a posture position sensor that can be attached to or secured in an article of clothing worn by the user.

It is yet another object of the present invention to provide a posture position sensor that will allow for backward or forward movement that deviates from upright or relaxed sitting positions for short selectable periods of time without triggering the alert means.

It is still another object of the present invention to provide a posture position sensor that the individual can easily set to define a preselected boundary of improper sitting positions so that when the user assumes an improper sitting position for a sufficient period of time within this preselected boundary, the alerting means will produce a signal to the user.

In accordance with these and other objects, the present invention includes a housing that contains an electrical circuit, an alerting means and a power means. The electrical circuit has a switch assembly and an electronic timer capable of being set at predetermined cycles. The switch assembly has a first conducting pendulum rotatably attached to the back wall of the housing and a second and third selectively positionable conducting pendulums pivotally attached to the housing back wall. The second and third pendulums have clamping means and conducting terminals removably secured to them. The second and third pendulums are manually positioned by set buttons located on the exterior of the housing which are associated with the clamping means. When an incorrect posture is assumed, the electrical circuit is opened by the first conducting pendulum which disengages with the terminals on the second or third pendulums and which causes the timer cycle to begin. When the preselected timer cycle elapses the alert means is activated to alert the user.

DETAILED DESCRIPTION OF THE INVENTION

The posture position sensor of the present invention produces a signal to alert the user of an incorrect sitting position. The operation of the device is based on the finding that a person's waist PATENT orientation determines in turn his or her spinal column curvature. Thus, it is preferable to attach the posture position sensor to the user's belt or pants by hooks, loops or clips such as "alligator" clips. The use of alligator clips is preferable because it is important to keep the posture position sensor stationary on the user's waist because of the acute sensitivity of the device.

In another embodiment, the posture position sensor can be used to monitor the chest position of the user for it too directly relates to the curvature of the spine. Thus, instead of being worn on the user's belt or pants, the sensor can be worn around the user's neck like a necklace. In this case the housing of the sensor would contain a rearranged switch assembly and a radio transmitter to activate the alert means. The alert means and power means could then be worn on the user's waist attached to the belt or pants or may be located at some preferred area such as inside the user's pocket. In lieu of utilizing a radio signal transmitter or receiver, the switch assembly may be wired to the alert means directly.

Figure 1:
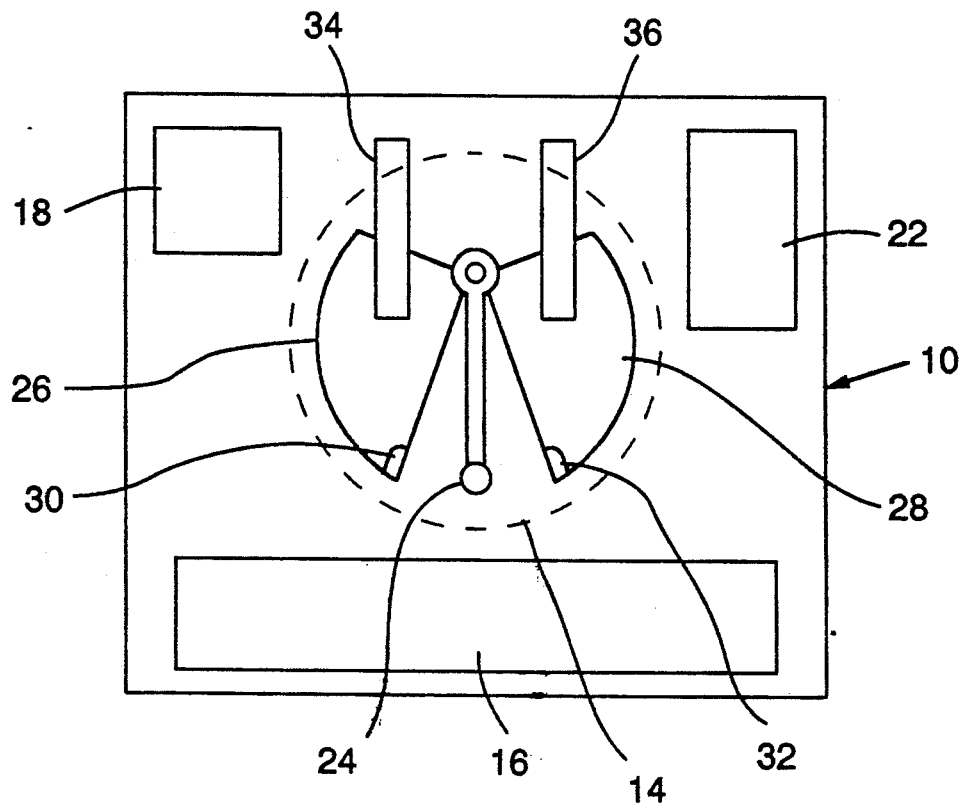
FIG. 1 is a plan view of the invention with the front cover of the housing removed so that the interior elements are exposed.

As shown in FIG. 1, the posture position sensor device of the present invention comprises a hollow housing 10 for receiving the various components of the device. In one embodiment, the housing 10 is quadrilateral in shape, but other shapes are possible. Further, the housing 10 may be constructed from any hard, rigid material. In a preferred embodiment, the housing 10 has a height of 2 inches, a width of 2 inches and a depth of one-half inch.

The individual components of the device contained within the housing 10 are connected in an electrical circuit. In one embodiment of the present invention, the electrical circuit has one point of interruption, the switch assembly 14. In another embodiment, the electrical circuit may have a second point of interruption between the power means 16 and the switch assembly 14. This second point of interruption is a power switch which controls the power supply to the device. The power switch is any type of on/off switch which is used to open and close the electrical circuit at the point of interruption between the power means 16 and the switch assembly 14. Each of the components of the present invention will now be described in detail.

As shown in FIG. 1, a power means 16 is located within the housing 10. Power means 16 may be secured to the housing by conventional means such as by a bracket. The means for securing the power means 16 to the housing has connectors for attaching wires which connect the power means 16 to the electrical circuit. The power means 16 may be a battery or any other type of small power supply sufficient to charge the timer 18. In a preferred embodiment, the power means 16 are two 1.5 volt AAA size batteries such as Energizer No. E92.

The timer 18 is a preferably a NE555 timer that is commonly available through Radio Shack or other electronic store(s). In actual practice, the conducting pendulum 24 of the switch assembly 14 described below is frequently thrown for very short periods of time. These frequent occurrences need to be screened out in order to prevent false alarms. To accomplish this, the timer can be manually set at various time cycles such that there is a preselected delay before the charged timer discharges and activates the alert means. This timer setting may be adjusted by the user based on personal preference or as may be dictated by the nature of the user's activities. For this reason, one embodiment of the present invention may utilize a timer set knob located on the exterior of the housing 10 for varying the timer delay setting.

The alert means 22 can be any type of low power component which is capable of producing a detectable signal such as a buzzer, beeper or a pager-type motor or vibrator. In a preferred embodiment, the alert means 22 is a coreless d.c. motor Model No. 7CE-1701 WL-00 that is commonly available through Namiki Precision of America, Inc. of Rochelle Park, N.J.

The switch assembly used in the posture position sensor is an "OR" type switch. As shown in FIG. 1, switch assembly 14 comprises a first conducting pendulum 24 which is rotatably attached to the back wall of the housing. The conducting pendulum 24 is a hanging, free swinging vertical pendulum which is one lead for the electrical circuit. The switch assembly 14 further comprises a second selectively-positionable conducting pendulum 26 and a third selectively-positionable conducting pendulum 28 which are pivotally attached to the back wall. Disposed on the second pendulum 26 is a first sensor terminal 30 which extends outwardly from the horizontal plane of the second pendulum 26 such that the first pendulum 24 closes the electrical circuit when it becomes engaged with the terminal 30. Similarly, disposed on the third pendulum 28 is a second sensor terminal 32 which extends outwardly from the horizontal plane of the third pendulum 28 such that the first pendulum 24 closes the electrical circuit when it becomes engaged with the terminal 32. The second and third pendulums 26 and 28 are not free swinging like the first conducting pendulum 24 because they are held in preselected stationary positions by clamping means as is discussed below.

The second and third pendulums constitute a lead for the electrical circuit when either the first or second terminal contacts the first pendulum 24. Thus, when the first conducting pendulum 24 is engaged with either of the sensor terminals 30 or 32 disposed on the second and third conducting pendulums 26 and 28, respectively, the switch assembly 14 is closed and the alert means 22 is not activated. When the first conducting pendulum 24 disengages with either of the sensor terminals 30 or 32, the switch assembly 14 opens and the preselected timer 18 cycle begins. If the switch assembly 14 is open for a period of time longer than the preselected timer cycle, the alert means 22 will activate and produce a signal to the user. The timer cycle is reset each time the conducting pendulum 24 touches either terminal 30 or 32. The circuitry of the timer 18 is more fully described below with reference to the circuit diagram of FIG. 3.

The sensor terminal 30 or 32 that is engaged with or disengaged from the pendulum 24 is dependent on whether the user's sitting position is beyond the boundary set by the user for the correct upright sitting position or the boundary set by the user for the correct reclined or relaxed sitting position. The procedure for setting the boundaries of correct sitting positions is described in more detail below.

Referring again to FIG. 1, removably secured to the second pendulum 26 and the third pendulum 28 are conducting clamping means 34 and 36 for selectively setting pendulums 26 and 28 at preselected stationary positions. These positions correspond to whatever the proper torso position of the user is while the user is sitting in the upright and relaxed sitting positions. When engaged with the pendulums 26 and 28, the conducting clamping means 34 and 36 restrict movement of the pendulums and prevent them from rotating about their axis. When the clamping means are disengaged, the pendulums 26 and 28 can freely swing about their axis. The pendulums 26 and 28 are rotated about their axis by interaction with first pendulum 24 which is moved by gravity. This allows the pendulums 26 and 28 to be set for various preselected sitting positions described above. Any deviation in the forward direction from either of these preselected sitting positions for a period of time longer than the timer cycle will cause the device to produce a signal to the user alerting the user of an incorrect sitting position.

The clamping means can be a coil spring or a spring tab made from any conducting material such that the clamping means can be engaged and disengaged with the pendulums 26 and 28. This allows the pendulums 26 and 28 to be selectively positioned by the user for different sitting positions as described above without having to disassemble or remove the sensor device from his or her waist.

Figure 2:
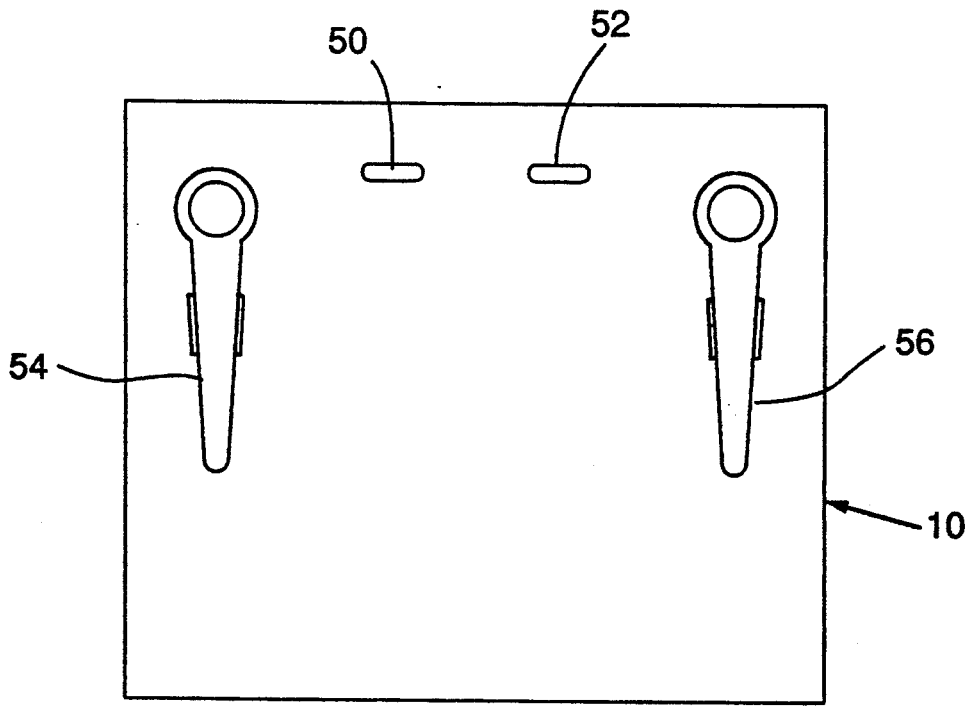
FIG. 2 is a plan view of the invention with the front cover secured thereto showing the set buttons and clips according to one embodiment.

The clamping means 34 and 36 are controlled by a two set buttons 50 and 52 located on the exterior of the housing 10 as seen in FIG. 2. Set button 50 is connected to the clamping means 34 and set button 52 is connected to the clamping means 36. When the user assumes a correct sitting position, whether upright or relaxed, and then presses set button 50, the clamping means 34 disengages from the second pendulum 26 thereby allowing it to be rotated about its axis by the first pendulum 24 under the action of gravity. Once the first pendulum 24 reaches the bottom of its gravitational swing and no longer causes the second pendulum 26 to rotate, the user releases the set button 50 which causes the clamping means 34 to engage with second pendulum 26 and lock it in place. The third pendulum 28 is set in the same manner using set button 52 which is connected to the clamping means 36.

Referring again to FIG. 2, the user attaches the device to his or her belt or pants using clips 54 and 56. If the user attaches the device to the right side of his or her waist, then the first set button 50 will be the front set button and the second set button 52 will be the rear set button. If the user attaches the device to the left side of his or her waist, the opposite designations apply.

The following description is for the situation in which the device is attached to the right side of the user's waist. To set for the proper upright sitting position, while sitting in the proper erect sitting position, the user depresses the first (front) set button 50. This will release the clamping means associated with this set button and allow the first pendulum to set the second pendulum. To set for a proper relaxed sitting position, while sitting in a proper relaxed position such as on a couch or in an automobile, the user depresses the second (rear) set button 52. This will release the clamping means associated with this set button and allow the first pendulum to set the third pendulum.

If the posture position sensor is worn on the left side of the waist, the same procedures for setting the device apply. However, in this embodiment, the front set button 50 becomes the rear set button 50 and the rear set button 52 becomes the front set button 52.

Further, FIG. 2 shows the set buttons 50 and 52 located on the side closest to the user. However, the set buttons can be located at any convenient, accessible place on the exterior of the housing.

Referring back to FIG. 1, the power means 16, the switch assembly 14, the timer 18 and the alert means 22 are connected by wires to form a complete electrical circuit. The wires are connected to the various components in conventional manner such as by soldering or clips.

Figure 3:
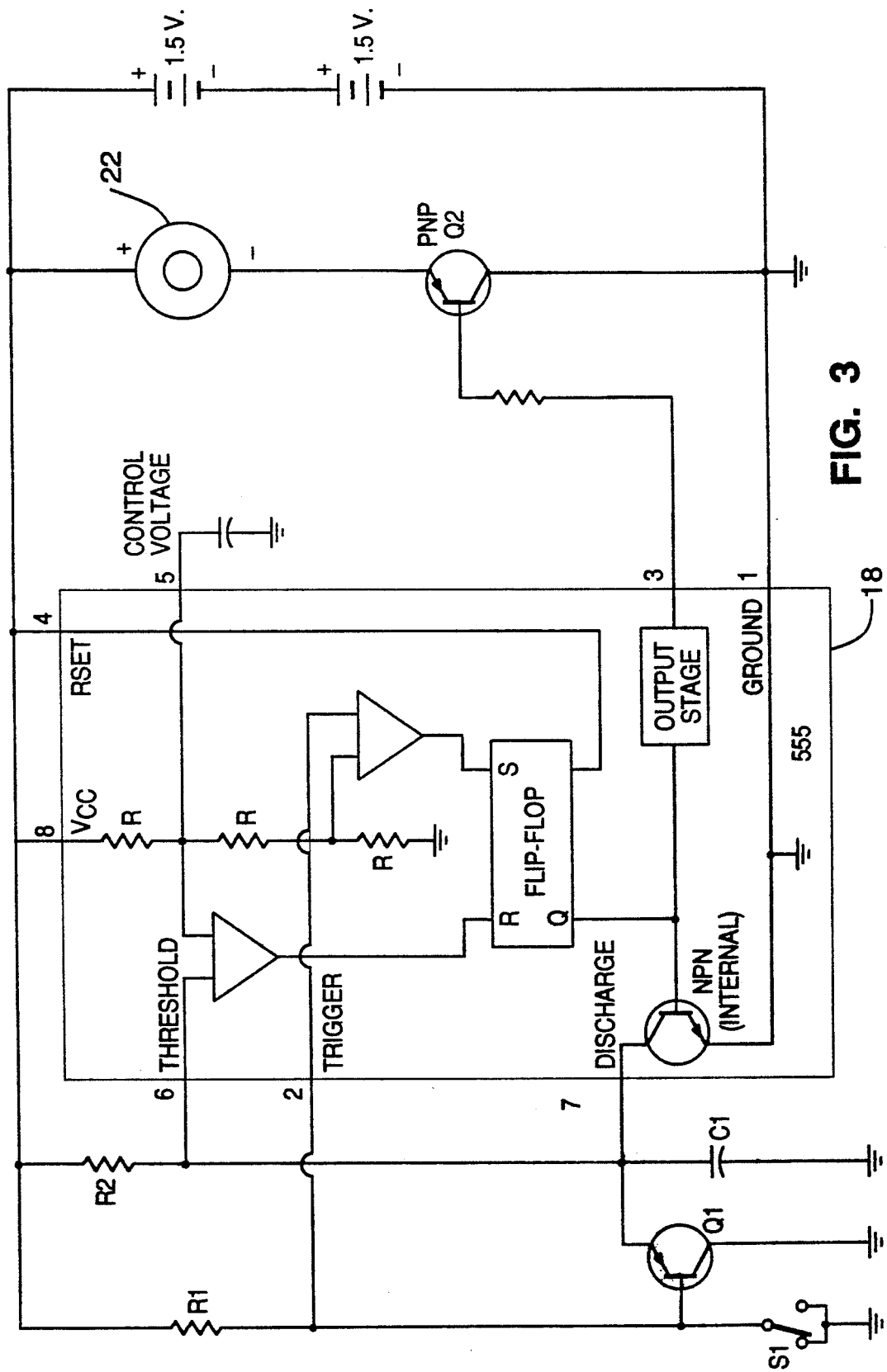
FIG. 3 is a generalized circuit diagram according to one embodiment of the present invention.

In order that the invention described herein may be more fully understood, FIG. 3, shows one embodiment of the electrical circuit connecting the individual components of the present invention. This figure is not intended to limit the scope of the invention in any manner as there are many other electrical schematics that can be used within the scope of the present invention. It will be obvious to those skilled in the art that many changes may be made in the described details of the preferred embodiment without departing from the underlying principles thereof.

As shown in FIG. 3, the electrical circuit of the presently preferred embodiment is configured with the well known NE555 timer and external components to perform the Event Failure Alarm function described in Forrest M. Mimms, III, *Engineer's Mini-Notebook* available at Radio Shack, the contents of which are incorporated herein by reference. The circuit includes a boost transistor Q2 which provides current drive for the alert means 22. When the user is in the proper sitting position, the switch assembly S1 is closed when in either of the closed positions. As long as S1 is closed, the circuit is in the following state; the transistor Q1 is open which prevents the capacitor C1 from charging, transistor Q2 remains off, and the alert means 22 remains inactivated. If the user temporarily assumes an improper sitting position, the switch assembly S1 will open, causing the transistor Q1 to turn off which will permit capacitor C1 to become charged through resistor R2. If the switch assembly S1 remains open for a period of time longer than the predetermined timer 18 cycle, the voltage across capacitor C1 will reach the threshold level at pin 6 of the timer 18 thereby causing the output pin 3 of the timer 18 to go from a high state to a low state. This low state at pin 3 of the timer 18 will cause the transistor Q2 to turn on thereby activating the alert means 22. However, if prior to the termination of the preselected timer 18 cycle the user returns to a proper sitting position, the switch assembly S1 will close and Q1 will turn on which will cause capacitor C1 to return to its discharged state. This will cause the output pin 3 to remain at a high state thereby preventing the alert means 22 from being activated. Although it is within the skill of the ordinary artisan to select the values of C1, C2, R1 and R1, it is preferable for C1=10 $\mu$F, C2=0.47 $\mu$F, R1=4.7M and R2=2.1M.

While the present invention has been described in detail by way of illustration and example for purposes of clarity of understanding, it is understood that certain changes and modifications may be made within the spirit of the invention and the scope of the appended claims.

What is claimed is:

1. A posture position sensor for attachment to a user's article of clothing for alerting the user whenever an incorrect posture position is assumed, said sensor comprising:

A) a housing;
B) an electrical circuit, said electrical circuit having;
  i) an electronic timer capable of being set at predetermined time cycles;
  ii) alert means to alert the user of an incorrect posture;
  iii) power means located within said housing to provide current to said electrical circuit;
  iv) a switch assembly including;
    (a) a first conducting pendulum rotatably fastened to a support member disposed within said housing;
    (b) a first conducting terminal disposed on a second selectively-positionable conducting pendulum pivotally attached to said support member, said second pendulum having conducting clamping means for selectively positioning said second pendulum in predetermined positions;
    c) a second conducting terminal disposed on a third selectively-positionable conducting pendulum pivotally attached to said support member, said third pendulum having conducting clamping means for selectively positioning said third pendulum in predetermined positions; wherein when said switch assembly is open, causing said predetermined electronic timer cycle to begin, said first conducting pendulum is disengaged from said first or second conducting terminals, wherein when said switch assembly is closed, causing said predetermined timer cycle to restart, said first conducting pendulum is disengaged from said first or second conducting terminals, and wherein said switch assembly allows said alert means to produce a signal only when said switch assembly is open for period of time longer than said predetermined timer cycle;
    c) a first set button connected to said second conducting pendulum clamping means for manually selecting the position of said second conducting pendulum; and
    d) a second set button connected to said third conducting pendulum for manually selecting the position of said third conducting pendulum.

2. The posture position sensor of claim 1 wherein said sensor housing further comprises means for attaching said sensor to a user's article of clothing.

3. The posture position sensor of claim 2 wherein said sensor attaching means comprises at least two alligator clips.

4. The posture sensor of claim 1 wherein said sensor further comprises an electronic timer cycle set knob.

5. The posture sensor of claim 1 wherein said sensor further comprises a power switch to manually control said power means to said sensor.

6. The posture sensor of claim 1 wherein said alert means is a vibrator motor.

7. The posture sensor of claim 1 wherein said alert means is a buzzer.

8. The posture sensor of claim 1 wherein said alert means is a beeper.

9. The posture sensor of claim 1 wherein said power means is a battery.

10. The posture sensor of claim 1 wherein said housing is two inches in height, two inches in width and one-half inch in depth.

* * * * *